United States Patent [19]

van de Werken

[11] Patent Number: Plant 7,535

[45] Date of Patent: May 28, 1991

[54] FORSYTHIA CV. 'LEMON-SCREEN'

[75] Inventor: Hendrik van de Werken, Knoxville, Tenn.

[73] Assignee: The University of Tennessee Research Corporation, Knoxville, Tenn.

[21] Appl. No.: 272,063

[22] Filed: Nov. 16, 1988

[51] Int. Cl.[5] ..... A01H 5/00
[52] U.S. Cl. ..... Plt./54
[58] Field of Search ..... Plt./54

[56] References Cited

U.S. PATENT DOCUMENTS

P.P. 6,655 3/1989 Hassinger ..... Plt. 54

OTHER PUBLICATIONS van de Werken (1988), "Mutant Offspring", *American Nurseryman*, vol. 167, No. 1 (Jan. 1, 1988), pp. 127–132.
Fincham, J., "Ionizing Radiation", *Genetics*, Jones and Bartlett Publishers, Inc., Boston, 1983, pp. 326–333.
Decourtye, L. (1978), "Utilisation de la Mutagenese pour l'Obtention de Nouvelles Varietes d'Arbustes Ornementaux", Comptes Rendus des Seances de l'Academie d'Agriculture de France, vol. 64(8), pp. 664–669.
"Arnoldia", vol. 31, No. 2, The Arnold Arboretum, Mar. 1971, pp. 41–63.
"Flowering Shrubs", Zucker, Isabel, 1966, D. Van Nostrand Co., Inc., New York, N.Y., p. 380.
"Hilliers Manual of Trees & Shrubs", 2nd American Edition, Hilliers & Sons Ltd., 1979, A. S. Barnes & Co., Cranbury, N.J., p. 575.
"Hortus Third, A Concise Dictionary of Plants Cultivated in the United States and Canada", 1976, MacMillan Publishing Co., New York, N.Y., p. 1290.
"Manual of Woody Landscape Plants—Their Identification, Ornamental Characteristics, Propagation and Uses", Dirr, Michael A., 1983, Stipes Publishing Co., Champaign, Ill., p. 826.

*Primary Examiner*—James R. Feyrer
*Attorney, Agent, or Firm*—William H. Elliott, Jr.

[57] ABSTRACT

A new cultivar of *Forsythia intermedia* named 'Lemon-Screen' characterized by its vigor, upright fan-shaped habit, lemon yellow flowers, high degree of sterility, its yellow shoots, and light green foliage.

2 Drawing Sheets

The invention relates to a new cultivar of *Forsythia intermedia* named "Lemon-Screen", which is characterized especially by its abundance of light yellow flowers, its sterility, yellow stems with chartreuse leaves in spring, and whitish blotches on otherwise normal green leaves in summer.

The new variety was derived from a periclinal chimera mutant, which itself was derived from a sectorial mutant, which was produced in turn by subjecting rooted cuttings of the parent *Forsythia intermedia* "Lynwood Gold" (a sport of *F. intermedia* "Spectabilis") to irradiation with 1,200 rad fast neutrons.

In 1968, three hundred cuttings of "Lynwood Gold" that had been potted and held in cold storage (38° F.) for six weeks and then returned to the greenhouse for two days were irradiated with 1200 rad fast neutrons. One of the plants of this group that broke dormancy formed a shoot with variegated foliage. This plant was cut back repeatedly to induce branching and eventually formed shoots that exhibited different characteristics. Each shoot was propagated by stem cuttings over 10 vegetative generations of selection and propagation. From this plant population two vegetatively selected types and three seedlings were selected. Further propagation and testing of these selections over several more years were shown to be the stable and new forsythia varieties that are the subject of this and four other copending plant patent applications; viz:

| Ser. No. | Name | Type |
|---|---|---|
| 272,063 | "Lemon-Screen" | vegetative selection |
| 273,489 | "Tinkle Bells" | vegetative selection |
| 271,919 | "Minikin" | seedling |
| 271,665 | "Fairy Land" | seedling |

-continued

| Ser. No. | Name | Type |
|---|---|---|
| 271,666 | "Pygmy-Red" | seedling |

Each differs greatly from the parent "Lynwood Gold" and also from one another.

"Lemon-Screen" was selected from a series of chimeral plants because of its distinct foliage, upright growth habit, and vigor. Cuttings from this plant have been rooted in soil and asexually propagated, and its progeny have displayed homogeneous and stable characteristics.

Throughout this specification, color names beginning with a small letter signify that the name of the color as used in common speech are aptly descriptive. Color names beginning with a capital letter designate values based on the R.H.S. Colour Chart, published by The Royal Horticultural Society of London, England.

The accompanying drawings illustrate the new variety in color as grown in Knox County within the State of Tennessee.

Figure 2:
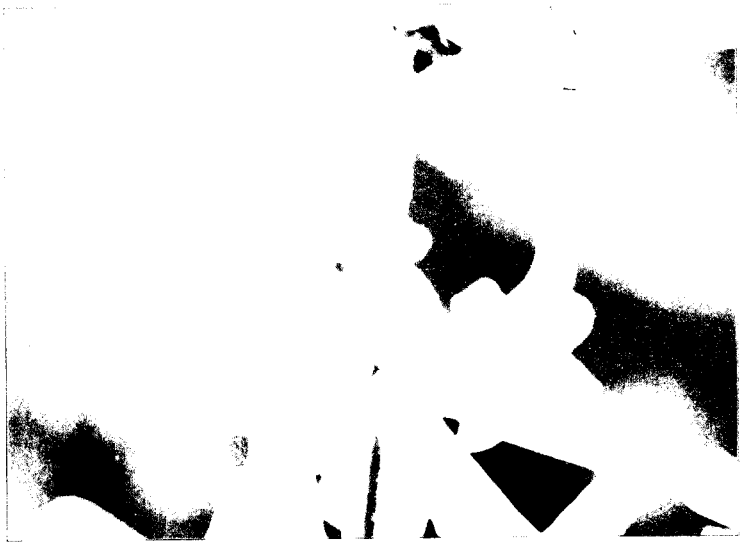
FIG. 2 is a close-up view of the flowers.
Figure 1:
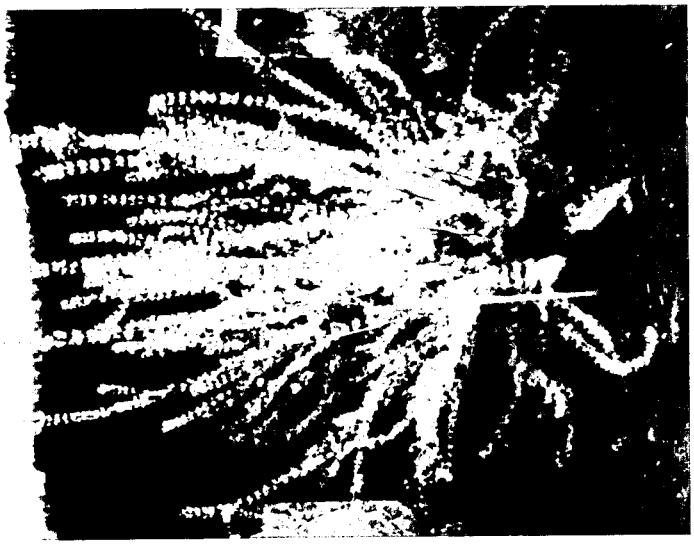
FIG. 1 illustrates 5½ year old "Lemon-Screen" in bloom in March-April.
Figure 3:
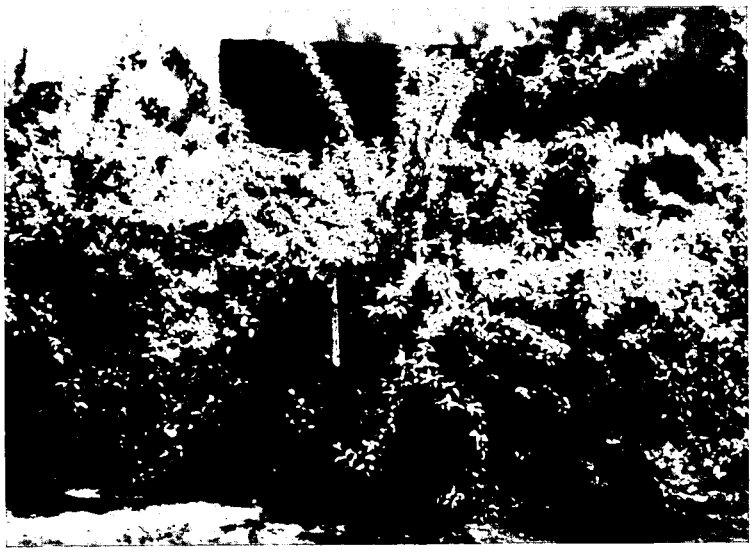
FIG. 3 illustrates the "Lemon-Screen" plant in leaf.
Figure 4:
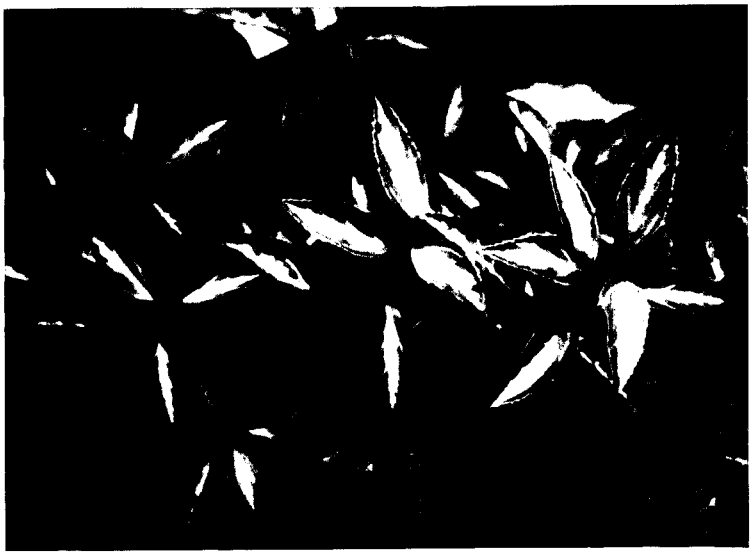
FIG. 4 is a closer view of the foliage shown in FIG. 3.

The following characteristics distinguish "Lemon-Screen" from its parent and other Forsythia cultivars:

THE PLANT

The "Lemon-Screen" plant form is tall and vigorous, with an upright, fan-shaped habit. "Lemon-Screen" ultimately reaches up to 10 ft. in height. The "Lemon- Screen" shrub is naturally open and graceful but is easily pruned as a tall, flowering screen in spring; it is hardy in Zone 6b or lower. Because of its vigor, "Lemon-Screen" is conveniently produced in the nursery field, but small plants can be grown in containers for a year if cut back substantially. The cultivar is particularly suited for landscape purposes, especially as a tall barrier or visual screen. "Lemon-Screen" will branch out quickly when vegetative shoots are pruned back, making the plant suitable in traffic or crash barriers, where dense plantings are used.

Its parent, "Lynwood Gold", by contrast is tall and slender—a straight upright variety with erect stems and which attains a height of 6 ft. to 7½ ft. at maturity.

FLOWER

"Lemon-Screen" has light lemon yellow flowers (Yellow 6C) that are 1½ in. to 1¾ in. in diameter. The internodes are 1" to 2" long on flowering wood. Flowering is early and profuse, with four and up to eight flowers per node on some portions of some stems. The corolla lobes are somewhat reflexed. Flowers have four petals and are sometimes fasciated. The flowers have aborted stamens and/or pistils; consequently, "Lemon-Screen" possesses a high degree of sterility.

The "Lynwood Gold" parent is fertile and has pistils that extend well above its pollen sacs, is late flowering and its medium sized flowers (about 1" to 1½" in diameter) are almost evenly spaced on the stem. The flowers of "Lynwood Gold" are brilliant yellow (lighter than its parent, F. Spectabilis). The corolla lobes of "Lynwood Gold" are reflexed and its petals are elliptic.

SHOOTS

The mature shoots of "Lemon-Screen" are yellow and pith is slightly lamellate between nodes.

The stems of the "Lynwood Gold" parent are green when young and brown when mature; they are a bit stiff; the pith at the nodes is lamellate, and on one year shoots, the stems between nodes are hollow.

FOLIAGE

The "Lemon-Screen" leaves are simple, serrate, acuminate at the tip, and attenuate at the base. The size of the leaves is not a distinguishing characteristic. The "Lemon-Screen" leaves which appear in the spring are chartreuse or of about a Yellow-Green 151 B color. In the summer the mature leaves are in the Yellow-Green 144 A/C range and have a Yellow-White 158 A, irregular blotch with no defined edge covering about 25-30% of the leaf surface and that extends outward from the mid rib and veins and contrasts with the green colored portions of the leaf. Fall foliage is Greyed Purple 156B. The summer foliage is disease and insect resistant. The young chartreuse leaves which appear after flowering are striking and suggest the plants are in bloom again. Summer pruning leads to the appearance of shoots with leaves that are chartreuse when young.

The leaves of the "Lynwood Gold" parent, on the other hand, are ovate lanceolate in shape and about 3" to 4½" long and about 1" to 1½" wide. Both young and old leaves are deep green in color.

To facilitate the comparison of the characteristics and features of "Lemon-Screen", the subject of this application, and its parent, "Lynwood Gold" and also with the four other new mutant offspring varieties of "Lynwood Gold" referred to above, there are attached hereto as Tables 1-5 comparative tabulations of the characteristics and properties of parent and its five offspring mutants that were developed from a single irradiated plant of "Lynwood Gold." Table 1 compares "Lemon-Screen" and its parent "Lynwood Gold". Table 2 compares "Lemon-Screen" and "Pygmy-Red". Table 3 compares "Lemon-Screen" and "Tinkle Bells". Table 4 compares "Lemon-Screen" and "Minikin". Table 5 compares "Lemon-Screen" and "Fairy Land".

TABLE 1

| | Ser. No. 272,063<br>LEMON SCREEN |
|---|---|
| Plant: | |
| Habit | Tall, open and graceful; Upright, fan shape; vigorous; open foliage |
| Size, height | up to 10' |
| Size, width | Hardy Zone 6b (or lower) |
| Vigor | Vigorous |
| Hardiness | |
| Productivity | Abundant Flowers/highly sterile/ pruned wood branches quickly |
| Stems or Shoots: | |
| Color (young) | |
| Color (mature) | Yellow |
| Rigidity | Slightly lamellate between nodes |
| Leaves: | |
| Type | Simple |
| Color: | |
| (young) | Yellow green 151 B or Chartreuse (appear after flowering) |
| (mature) | Normal green (Yellow-Green 144) whitish blotches |
| (fall) | Greyed Purple 187 B |
| Shape | |
| tip | Accuminate |
| base | Attenuate |
| margins | Serrate |
| Size | |
| length | Not distinguishing |
| width | Not distinguishing |
| Venation | Pinnate |
| Flower: | |
| Date of Flowering | Early |
| Size: width | 1½"-1¾" |
| Color: | Yellow (6 C) |
| Corolla: | |
| length | |
| lobes | Somewhat reflexed |
| Petals: number | 4, sometimes fasciated |
| Pistils: | aborted stamens &/or pistils |
| Number per node: | 4 to 8 |
| Insertion angle on upright stems: | |
| Internodes: | 1" to 2" long on flowering wood |
| Stress Resistance: | Summer foliage disease & insect resistant |
| Utility Aspects: | Summer pruning leads to shoot with chartreuse leaves (young) |
| | LYNWOOD GOLD |
| Plant: | |
| Habit | Tall, slender-Upright straight & erect stems |
| Size, height | 6'-7½' |
| Size, width | |
| Vigor | |
| Hardiness | |
| Productivity | Fertile |
| Stems or Shoots: | |
| Color (young) | Green |
| Color (mature) | Brown |
| Rigidity | A bit stiff; pith nodes lamellate; hollow between nodes on one year shoots |
| Leaves: | |
| Type | |
| Color: | |
| (young) | Deep Green |

TABLE 1-continued

| | |
|---|---|
| (mature) | Deep Green |
| (fall) | |
| Shape | ovate lanceolate |
| tip | |
| base | |
| margins | |
| Size | |
| length | 3–4½" |
| width | 1–1½" |
| Venation | |
| Flower: | |
| Date of Flowering | Late |
| Size: width | 1"–1¼" (medium) |
| Color: | Brillant Yellow (lighter than its paren Spectabilis) |
| Corolla: | |
| length | |
| lobes | Reflexed |
| Petals: number | Large, broad, open |
| | Elliptic |
| Pistils: | Extend well above pollen sacs (anthers) of stamens |
| Number per node: | |
| Insertion angle on upright stems: | |
| Internodes: | Flowers almost evenly spaced on stems |
| Stress Resistance: | |
| Utility Aspects: | |

TABLE 2

| | Ser. No. 272,063 LEMON SCREEN |
|---|---|
| Plant: | |
| Habit | Tall, open and graceful; Upright, fan shape; vigorous; open foliage |
| Size, height | up to 10' |
| Size, width | Hardy Zone 6b (or lower) |
| Vigor | Vigorous |
| Hardiness | |
| Productivity | Abundant Flowers/highly sterile/ pruned wood branches quickly |
| Stems or Shoots: | |
| Color (young) | |
| Color (mature) | Yellow |
| Rigidity | Slightly lamellate between nodes |
| Leaves: | |
| Type | Simple |
| Color: | |
| (young) | Yellow green 151 B or Chartreuse (appear after flowering) |
| (mature) | Normal green (Yellow-Green 144) whitish blotches |
| (fall) | Greyed Purple 187 B |
| Shape | |
| tip | Accuminate |
| base | Attenuate |
| margins | Serrate |
| Size | |
| length | Not distinguishing |
| width | Not distinguishing |
| Venation | Pinnate |
| Flower: | |
| Date of Flowering | Early |
| Size: width | 1½"–1¾" |
| Color: | Yellow (6 C) |
| Corolla: | |
| length | |
| lobes | Somewhat reflexed |
| Petals number | 4, sometimes fasciated |
| Pistils: | aborted stamens &/or pistils |
| Number per node: | 4 to 8 |
| Insertion angle on upright stems: | |
| Internodes: | 1" to 2" long on flowering wood |

TABLE 2-continued

| | |
|---|---|
| Stress Resistance: | Summer foliage disease & insect resistant |
| Utility Aspects: | Summer pruning leads to shoot with chartreuse leaves (young) |

| | Ser. No. 271,666 PYGMY RED |
|---|---|
| Plant: | |
| Habit | Low, loose graceful arching to ground |
| Size, height | 3½'–4½' |
| Size, width | 5'–6' |
| Vigor | Good vigor |
| Hardiness | Hardy Zone 6b (or lower) |
| Productivity | Readily roots where branches touch ground few seed pods |
| Stems or Shoots: | |
| Color (young) | High anthocyanin |
| Color (mature) | Purple Red (59 A) |
| Rigidity | Flexible lamellate between nodes |
| Leaves: | |
| Type | Simple |
| Color: | |
| (young) | Dark Green |
| (mature) | Dark Green |
| (fall) | Anthocyanin (maroon) expressed in full sun |
| Shape | Lanceolate (few lobed leaves on vegetative shoots) |
| tip | Accuminate |
| base | Attenuate |
| margins | Serrate |
| Size | |
| length | 2"–2½" on flowering wood; to 2¾" on vegatative wood |
| width | 0.3"–0.4" on flowering wood; to 1" on vegetative wood |
| Venation | Pinnate |
| Flower: | |
| Date of Flowering | Intermediate |
| Size: width | 1¼"–1½" |
| Color: | Yellow (7A) |
| Corolla: | |
| length | |
| lobes | Narrow |
| Petals number | 4 - sometimes 5 |
| Pistils: | Extend 2/25"–3/25" above pollen sacs of stamens |
| Number per node: | 2 |
| Insertion angle on upright stems: | |
| Internodes: | 1"–1½" (1½" even on fast growing shoots |
| Stress Resistance: | disease and insect |
| Utility Aspects: | |

TABLE 3

| | Ser. No. 272,063 LEMON SCREEN |
|---|---|
| Plant: | |
| Habit | Tall, open and graceful; Upright, fan shape; vigorous; open foliage |
| Size, height | up to 10' |
| Size, width | Hardy Zone 6b (or lower) |
| Vigor | Vigorous |
| Hardiness | |
| Productivity | Abundant Flowers/highly sterile/ pruned wood branches quickly |
| Stems or Shoots: | |
| Color (young) | |
| Color (mature) | Yellow |
| Rigidity | Slightly lamellate between nodes |
| Leaves: | |
| Type | Simple |
| Color: | |

TABLE 3-continued

| | |
|---|---|
| (young) | Yellow green 151 B or Chartreuse (appear after flowering) |
| (mature) | Normal green (Yellow-Green 144) whitish blotches |
| (fall) | Greyed Purple 187 B |
| Shape | |
| tip | Accuminate |
| base | Attenuate |
| margins | Serrate |
| Size | |
| length | Not distinguishing |
| width | Not distinguishing |
| Venation | Pinnate |
| Flower: | |
| Date of Flowering | Early |
| Size: width | 1½"-1¾" |
| Color: | Yellow (6 C) |
| Corolla: | |
| length | |
| lobes | Somewhat reflexed |
| Petals number | 4, sometimes fasciated |
| Pistils: | aborted stamens &/or pistils |
| Number per node: | 4 to 8 |
| Insertion angle on upright stems: | |
| Internodes: | 1" to 2" long on flowering wood |
| Stress Resistance: | Summer foliage disease & insect resistant |
| Utility Aspects: | Summer pruning leads to shoot with chartreuse leaves (young) |

| | Ser. No. 273,489 TINKLE BELLS |
|---|---|
| Plant: | |
| Habit | Semi-dwarf; Upright |
| Size, height | 4'-4½' |
| Size, width | |
| Vigor | Medium vigor |
| Hardiness | Hardy Zone 6b (or lower) |
| Productivity | Does not layer naturally (replicates from stools (no seed pods observed) |
| Stems or Shoots: | |
| Color (young) | Yellow Green |
| Color (mature) | Light brown |
| Rigidity | Sparsely lamellate between nodes - Rigid |
| Leaves: | |
| Type | Simple |
| Color: | |
| (young) | Medium Green |
| (mature) | Medium Green |
| (fall) | Faded green to yellow |
| Shape | Elliptical |
| tip | Acute on flower shoots accuminate on vegetative shoots |
| base | |
| margins | serrate on upper ⅓ near tip |
| Size | |
| length | 2"-3" (with petiole) |
| width | ½" |
| Venation | Pinnate |
| Flower: | |
| Date of Flowering | Early |
| Size: width | ½"-¾" at 45° angle |
| Color: | Bright Yellow (7 B) |
| Corolla: | |
| length | ½" open to 45° angle |
| lobes | not reflexed during prime |
| Petals number | 4; occasionally 5 or 6 |
| Pistils: | short: anthers slightly below stigma portion of pistil |
| Number per node: | 2; often 4 per node |
| Insertion angle on upright stems: | buds & flowers pendulous |
| Internodes: | ½—1½" |
| Stress Resistance: | Disease and insect |
| Utility Aspects: | Can force flowering suitable for container culture |

TABLE 4

| | Ser. No. 272,063 LEMON SCREEN |
|---|---|
| Plant: | |
| Habit | Tall, open and graceful; Upright, fan shape; vigorous; open foliage |
| Size, height | Up to 10' |
| Size, width | Hardy Zone 6b (or lower) |
| Vigor | Vigorous |
| Hardiness | |
| Productivity | Abundant Flowers/highly sterile/ pruned wood branches quickly |
| Stems of Shoots: | |
| Color (young) | |
| Color (mature) | Yellow |
| Rigidity | Slightly lamellate between nodes |
| Leaves: | |
| Type | Simple |
| Color: | |
| (young) | Yellow green 151 B or Chartreuse (appear after flowering) |
| (mature) | Normal green (Yellow-Green 144) whitish blotches |
| (fall) | Greyed Purple 187 B |
| Shape | |
| tip | Accuminate |
| base | Attenuate |
| margins | Serrate |
| Size | |
| length | Not distinguishing |
| width | Not distinguishing |
| Venation | Pinnate |
| Flower: | |
| Date of Flowering | Early |
| Size: width | 1½"-1¾" |
| Color: | Yellow (6 C) |
| Corolla: | |
| length | |
| lobes | Somewhat reflexed |
| Petals: number | 4, sometimes fasciated |
| Pistils: | aborted stamens &/or pistils |
| Number per node: | 4 to 8 |
| Insertion angle on upright stems: | |
| Internodes: | 1" to 2" long on flowering wood |
| Stress Resistance: | Summer foliage disease & insect resistant |
| Utility Aspects: | Summer pruning leads to shoot with chartreuse leaves (young) |

| | Ser. No. 271,919 MINIKIN |
|---|---|
| Plant: | |
| Habit | Small stature, fine textured; small leaves and small stems; densely foliated |
| Size, height | 2'-2½' |
| Size, width | 3'-4' |
| Vigor | Good vigor but slow growth |
| Hardiness | Zone 6b (or lower) |
| | Layers naturally |
| Productivity | Abundant seed pods |
| Stems or Shoots: | |
| Color (young) | Light green |
| Color (mature) | Brownish green |
| | Ascending strongly |
| Rigidity | lamellate between nodes |
| Leaves: | |
| Type | Simple |
| Color: | |
| (young) | Bright green to dark green |
| (mature) | Bright green to dark green |
| (fall) | Fading green until leaf drop |

TABLE 4-continued

| | |
|---|---|
| Shape | Linear |
| tip | Accuminate |
| base | Attenuate |
| margins | Lightly serrate |
| Size: | |
| length | On vegetative shoots - 1½" attached to ½" long slender petiole; smaller on flowering shoots |
| width | On vegetative shoots - ¼"; |
| Venation | Pinnate |
| Flower: | |
| Date of Flowering | Intermediate |
| Size: width | ½"-¾" (cup shaped) fully reflexed |
| Color: | Yellow (9 A) |
| Corolla: | |
| length | |
| lobes | strongly reflexed, very small |
| Petals: number | 4:- short and recurved |
| Pistils: | Short; 1/25" below pollen sacs of stamens |
| Number per node: | 2-4 |
| Insertion angle on upright stems: | |
| Internodes: | Short (Flowering shoots ¼"-¾" Vegetative shoots up to 2") |
| Stress Resistance: | Doesn't require same degree of winter protection as most container grown plants of genre |
| Utility Aspects: | Blooming can be forced. Especially suited for container culture. |

TABLE 5

| | Ser. No. 272,063 LEMON SCREEN |
|---|---|
| Plant: | |
| Habit | Tall, open and graceful; Upright, fan shape; vigorous; open foliage |
| Size, height | Up to 10' |
| Size, width | Hardy Zone 6b (or lower) |
| Vigor | Vigorous |
| Hardiness | |
| Productivity | Abundant Flowers/highly sterile/ pruned wood branches quickly |
| Stems of Shoots: | |
| Color (young) | |
| Color (mature) | Yellow |
| Rigidity | Slightly lamellate between nodes |
| Leaves: | |
| Type | Simple |
| Color: | |
| (young) | Yellow green 151 B or Chartreuse (appear after flowering) |
| (mature) | Normal green (Yellow-Green 144) whitish blotches |
| (fall) | Greyed Purple 187 B |
| Shape | |
| tip | Accuminate |
| base | Attenuate |
| margins | Serrate |
| Size | |
| length | Not distinguishing |
| width | Not distinguishing |
| Venation | Pinnate |
| Flower: | |
| Date of Flowering | Early |
| Size: width | 1½"-1¾" |

TABLE 5-continued

| | |
|---|---|
| Color: | Yellow (6 C) |
| Corolla: | |
| length | |
| lobes | Somewhat reflexed |
| Petals: number | 4, sometimes fasciated |
| Pistils: | aborted stamens &/or pistils |
| Number per node: | 4 to 8 |
| Insertion angle on upright stems: | |
| Internodes: | 1" to 2" long on flowering wood |
| Stress Resistance: | Summer foliage disease & insect resistant |
| Utility Aspects: | Summer pruning leads to shoot with chartreuse leaves (young) |

| | Ser. No. 271,665 FAIRY LAND |
|---|---|
| Plant: | |
| Habit | Small overal & fine textured: Closely spaced flowers & leaves Dense (young) foliage |
| Size, height | 3'-4' |
| Size, width | 5'-6' |
| Vigor | Good vigor for size |
| Hardiness | Zone 6b (or lower) |
| Productivity | Few seed pods |
| Stems or Shoots: | |
| Color (young) | Light green |
| Color (mature) | Brownish green |
| Rigidity | Very flexible lamellate between nodes |
| Leaves: | |
| Type | Simple |
| Color: | |
| (young) | Medium green (fairly light) |
| (mature) | Medium green (fairly light) |
| (fall) | Mostly faded yellow |
| Shape | Lanceolate |
| tip | Accuminate |
| base | Attenuate |
| margins | On flowering wood; entire On vegetative wood: serrate top ⅓ |
| Size: | |
| length | On flowering wood: - 1½"-2½" On vegetative shoots: about 3" |
| width | On flowering wood: 0.2"-0.4" On vegetative shoots 0.5-0.6" |
| Venation | Pinnate |
| Flower: | |
| Date of Flowering | Intermediate |
| Size: width | ¾"-1¼" |
| Color: | Yellow (6 A) |
| Corolla: | |
| length | |
| lobes | Reflexed, small |
| Petals: number | Generally 4-many have 5, 6, 7 and 8 on single corolla |
| Pistils: | Extend 3/25" to 4/25" above pollen sacs (anthers) of the stamen |
| Number per node: | 2-4 |
| Insertion angle on upright stems: | |
| Internodes: | ¼" to about 1" |
| Stress Resistance: | |
| Utility Aspects: | Very well suited for container culture. |

What is claimed is:

1. A new and distinct cultivar of *Forsythia intermedia* named 'Lemon-Screen' substantially as shown and described herein.

* * * * *